(12) United States Patent
Knochel et al.

(10) Patent No.: US 7,235,696 B2
(45) Date of Patent: Jun. 26, 2007

(54) CHIRAL DIPHOSPHINOTERPENES AND TRANSITION METAL COMPLEXES THEREOF

(75) Inventors: Paul Knochel, Gauting (DE); Tanasari Bunlaksananusorn, Leverkusen (DE); Andrei Gavryushin, Germering (DE)

(73) Assignee: Lanxess Deutschland GmbH, Leverkusen (DE)

( * ) Notice: Subject to any disclaimer, the term of this patent is extended or adjusted under 35 U.S.C. 154(b) by 49 days.

(21) Appl. No.: 11/125,376

(22) Filed: May 9, 2005

(65) Prior Publication Data

US 2005/0267316 A1 Dec. 1, 2005

(30) Foreign Application Priority Data

May 10, 2004 (DE) .................. 10 2004 022 898

(51) Int. Cl.
*C09F 9/02* (2006.01)
*C07F 15/00* (2006.01)
*B01J 31/00* (2006.01)

(52) U.S. Cl. .................. 568/10; 502/162; 556/21; 568/14

(58) Field of Classification Search .......... 556/21; 568/17, 10, 14; 502/162
See application file for complete search history.

(56) References Cited

OTHER PUBLICATIONS

Organometallics, 1990, 9, pp. 273-275, R. L. Halterman et al, "Stereoselective Formation of ($C_S$-Symmetrical π-allyl)palladium Complexes".
Demay S et al: "Stereoselective Preparation of Phosphine Oxides via a 2,3-Sigmatropic Shift of Allylic Diphenylphosphinites" Tetrahedron Letters, Elsevier Science Publishers, Amsterdam, NL. Bd. 40, Nr. 27, 2. Juli 1999 (Jul. 2, 1999), Seiten 4981-4984, XP004169375 ISSN: 0040-4039 * das ganze Dokument *.
Demay S. et al.: New C2-symmetrical 1,2-diphosphanes for the efficient rhodium-catalyzed asymmetric hydroboration of styrene derivatives: Angewandte Chemie. International Edition., Bd. 40, Nr. 7, 2001, Seiten 1235-1238, XP002339814 De Verlag Chemie. Weinheim. * das ganze Dokument *.
Gavryushin A et al: "Novel chiral diphosphine ligands with a pinene core obtained via an allylphosphinite-allylphosphine oxide rearrangement" Tetrahedron: Asymmetry, Elsevier Science Publishers, Amsterdam, NL. Bd. 15, Nr. 14, 26. Juli 2004 (Jul. 26, 2004), Seiten 2279-2288, XP004523720 ISSN: 0957-4166 * das ganze Dokument *.

*Primary Examiner*—Porfirio Nazario-Gonzalez
(74) *Attorney, Agent, or Firm*—Michael A. Miller

(57) ABSTRACT

The present invention relates to chiral diphosphinoterpenes and transition metal complexes thereof, to a process for preparing chiral diphosphinoterpenes and oxides thereof, and to transition metal complexes comprising the chiral diphosphinoterpenes. In a further aspect, the invention relates to the use of the chiral diphosphinoterpenes or transition metal complexes thereof in asymmetric syntheses.

9 Claims, No Drawings

CHIRAL DIPHOSPHINOTERPENES AND TRANSITION METAL COMPLEXES THEREOF

The present invention relates to chiral diphosphinoterpenes and transition metal complexes thereof, to a process for preparing chiral diphosphinoterpenes and oxides thereof. In a further aspect, the invention relates to the use of the chiral diphosphinoterpenes or transition metal complexes thereof in asymmetric syntheses.

Enantiomerically enriched chiral compounds are valuable starting substances for preparing agrochemicals and pharmaceuticals. The asymmetric catalysis for the synthesis of such enantiomerically enriched chiral compounds has gained great industrial significance.

The multitude of publications in the field of asymmetric synthesis shows clearly that transition metal complexes of diphosphorus compounds are particularly suitable as catalysts in asymmetrically controlled reactions. In particular, transition metal complexes of diphosphorus compounds have found use in industrial processes in asymmetric hydrogenations of C=O, C=N and C=C bonds, hydrocyanations and hydroformylations.

Haltermann, Organometallics, 9, (1), 1990, pp. 273-275 discloses (2R,3S)-2-[(diphenylphosphinyl)methyl]-3-diphenylphosphinylbicyclo[3.3.1]heptane and a palladium complex preparable therefrom. No information is given about use in asymmetric synthesis.

There is a need to develop a ligand system which can be varied readily in its steric and electronic properties, and whose transition metal complexes as catalysts in asymmetric synthesis, in particular asymmetric hydrogenations, enable not only high enantioselectivity but also high turnover rates. In addition, there is a need to develop a convenient route for such a ligand system and the corresponding precursors.

Compounds of the formula (I) have now been found

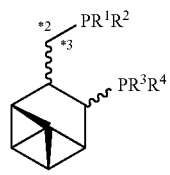

(I)

in which
*2 and *3 each mark a stereogenic carbon atom which is in R- or S-configuration, although the substituents are arranged in a cisoid manner based on the connecting carbon bond and
$R^1$, $R^2$, $R^3$ and $R^4$ may each independently be: alkyl, arylalkyl or aryl or a heterocyclic radical having a total of 4 to 16 carbon atoms, or $R^1$ and $R^2$ and/or $R^3$ and $R^4$ each together are alkylene.

The scope of the invention encompasses all radical definitions, parameters and illustrations above and cited hereinbelow, in general or within areas of preference, in any combination with one another, i.e. also between the particular areas and areas of preference.

In the context of the invention, unless stated specifically, aryl is preferably carbocyclic aromatic radicals having 6 to 24 skeleton carbon atoms or heteroaromatic radicals having 5 to 24 skeleton carbon atoms, in which no, one, two or three skeleton carbon atoms per cycle, but at least one skeleton carbon atom in the entire molecule, may be substituted by heteroatoms selected from the group of nitrogen, sulphur or oxygen. In addition, the carbocyclic aromatic radicals or heteroaromatic radicals may be substituted by up to five identical or different substituents per cycle, selected from the group of hydroxyl, fluorine, nitro, cyano, free and protected formyl, $C_1$-$C_{12}$-alkyl, $C_5$-$C_{14}$-aryl, $C_6$-$C_{15}$-arylalkyl, —PO—[($C_1$-$C_8$)-alkyl]$_2$, —PO—[($C_5$-$C_{14}$)-aryl]$_2$, —PO—[($C_1$-$C_8$)-alkyl)($C_5$-$C_{14}$)-aryl)], tri($C_1$-$C_8$-alkyl)siloxyl and radicals of the formulae (IIa) to (IIf). The same applies to the aryl moiety of an aryl-alkyl radical.

For example, aryl is more preferably phenyl, naphthyl or anthracenyl, each of which is optionally mono-, di- or trisubstituted by radicals which are each independently selected from the group of $C_1$-$C_6$-alkyl, $C_5$-$C_{14}$-aryl, $C_1$-$C_6$-alkoxy, $C_1$-$C_6$-alkoxy-carbonyl, halogen, hydroxyl, nitro or cyano.

In the context of the invention, unless stated specifically, alkyl, alkylene and alkoxy are preferably each independently a straight-chain, cyclic, branched or unbranched alkyl, alkylene and alkoxy radical respectively, each of which may optionally be further substituted by $C_1$-$C_4$-alkoxy radicals. The same applies to the alkylene moiety of an arylalkyl radical.

For example, alkyl is more preferably methyl, ethyl, n-propyl, isopropyl, n-butyl, tert-butyl, n-pentyl, cyclohexyl and n-hexyl, n-heptyl, n-octyl, isooctyl, n-decyl and n-dodecyl.

For example, alkylene is preferably 1,3-propylene, 1,4-butylene, 1,5-pentylene, 1,6-hexylene, S,S- or R,R-2,5-hexylene, 1,4-cyclohexylene, 1,2-cyclohexylene and 1,8-octylene.

For example, alkoxy is preferably methoxy, ethoxy, isopropoxy, n-propoxy, n-butoxy, tert-butoxy and cyclohexyloxy.

In the context of the invention, unless stated specifically, arylalkyl is preferably in each case independently a straight-chain, cyclic, branched or unbranched alkyl radical which is mono- or polysubstituted, more preferably monosubstituted, by aryl radicals as defined above.

In the context of the invention, unless stated specifically, haloalkyl and haloalkylene are preferably in each case independently a straight-chain, cyclic, branched or unbranched alkyl and alkylene radical respectively, each of which may be substituted once, more than once or fully by halogen atoms each selected independently from the group of fluorine, chlorine, bromine and iodine.

For example, haloalkyl is more preferably trifluoromethyl, trichloromethyl, 2,2,2-trifluoroethyl, pentafluoroethyl and nonafluorobutyl; $C_1$-$C_8$-fluoroalkyl is more preferably trifluoromethyl, 2,2,2-trifluoroethyl, pentafluoroethyl and nonafluorobutyl.

Preferred compounds of the formula (I) are defined hereinbelow.

The compounds of the formula (I) are preferably enantiomerically enriched.

$R^1$ and $R^2$ or $R^3$ and $R^4$ are preferably, in each case in pairs and identically: alkyl or aryl or a heterocyclic radical having a total of 4 to 9 carbon atoms or, in each case together, alkylene.

More preferably, $R^1$ and $R^2$ or $R^3$ and $R^4$, in each case as a pair and identically, are: $C_3$-$C_6$-alkyl, optionally mono-, di- or tri-$C_1$-$C_6$-alkyl-, —$C_1$-$C_6$-haloalkyl-, —$C_1$-$C_6$-alkoxy-, -chlorine- or -fluorine-substituted phenyl or, in each case together, are $C_4$-$C_6$-alkylene. Very particular preference is given to all four radicals $R^1$, $R^2$, $R^3$ and $R^4$ being identical.

Very particularly preferred compounds of the formula (I) are:

(2S,3S)-3-diphenylphosphinyl-2-[(diphenylphosphinyl)methyl]-6,6-dimethylbicyclo -[3.1.1]heptane, (2R,3R)-3-diphenylphosphinyl-2-[(diphenylphosphinyl)methyl]-6,6-dimethylbicyclo[3.1.1]heptane, (2R,3R)-3-diphenylphosphinyl-2-[(diphenylphosphinyl)methyl]-6,6-dimethylbicyclo[3.1.1]heptane and (2R,3R)-3- diphenylphosphinyl 2-[(diphenylphosphinyl)methyl]-6,6-dimethylbicyclo[3.1.1]heptane.

In addition, the invention also embraces complexes of compounds of the formula (I) with boranes, for example borane or borabicyclononane (BBN-9).

In the context of the invention, the terms stereoisomerically enriched and enantiomerically enriched include stereoisomerically pure and enantiomerically pure compounds and mixtures of stereoisomeric or enantiomeric compounds in which one stereoisomer or enantiomer is present in a larger relative proportion than the other stereoisomer(s) or enantiomer(s), preferably in a relative proportion of above 50% to 100 mol %, more preferably 90 to 100 mol % and most preferably 98 to 100 mol %.

The compounds of the formula (I) can be prepared by a process which likewise forms part of the subject-matter of the invention.

This process is characterized in that in a step A), compounds of the formula (IIa) or (IIb)

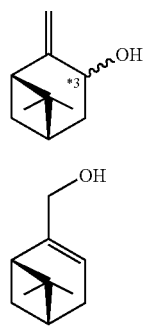

(IIa)

(IIb)

in which *3 has the definitions and areas of preference specified for formula (I)

are reacted with compounds of the formula (IIIa) or (IIIb)

Hal-PR$^1$R$^2$ (IIIa)

Hal-PR$^3$R$^4$ (IIIb)

to give compounds of the formula (IVa) and (IVb)

(IVa)

(IVb)

and in a step B), the compounds of the formula (IVa) and (IVb), optionally in an organic solvent, are converted by heating to at least 60° C. to compounds of the formula (Va) and (Vb)

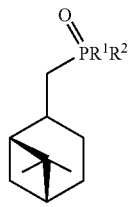

(Va)

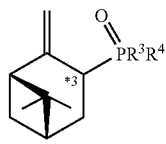

(Vb)

and, in a step C), the compounds of the formula (Va) and (Vb) are converted by reacting with a borane and subsequently oxidizing to compounds of the formula (VIa) and (VIb)

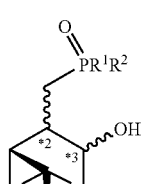

(VIa)

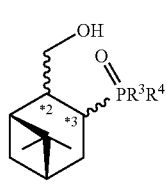

(VIb)

and, in a step D), the compounds of the formula (VIa) and (VIb) are converted by reducing to compounds of the formula (VIIa) and (VIIb)

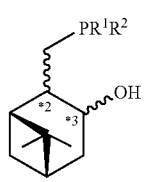

(VIIa)

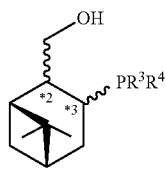

(VIIb)

and, in a step E), the compounds of the formula (VIIa) and (VIIb) are converted by reacting with compounds of the formula (VIII)

Hal-O$_2$SR$^5$ (VIII)

to compounds of the formula (IXa) and (IXb)

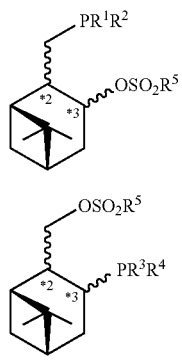

(IXa)

(IXb)

and, in a step F), the compounds of the formula (IX) are converted by reacting with compounds of the formula (Xa) or (Xb)

HPR³R⁴ (Xa)

HPR¹R² (Xb)

to the compounds of the formula (I).

In the formulae (IIa), (IIb), (IIIa), (IIIb), (IVa), (IVb), (Va), (Vb), (VIa), (VIb), (VIIa), (VIIb), (IXa), (IXb), (Xa) and (Xb), *2 and *3, $R^1$, $R^2$, $R^3$ and $R^4$ each have the same definitions and areas of preference as have already been described under the formula (I).

Moreover, $R^5$ in the formulae (VIII), (IXa) and (IXb) is alkyl, fluoroalkyl, arylalkyl or aryl, preferably alkyl and fluoroalkyl.

In the formulae (IIIa) and (IIIb) and (VIII), Hal is in each case chlorine, bromine or iodine, preferably chlorine.

The compounds of the formulae (IVa), (IVb), (Va), (Vb), (VIa), (VIb), (VIIa), (VIIb), (IXa) and (IXb) are hitherto unknown and are therefore encompassed by the invention as indispensible intermediates. The abovementioned definitions and areas of preference for *1, *2 and *3, $R^1$, $R^2$, $R^3$, $R^4$ and $R^5$ apply in the same manner.

Also encompassed by the invention are complexes of compounds of the formula (VIIa) and (VIIb) with boranes, for example borane or borabicyclononane (BBN-9).

The invention further provides processes which comprise the steps below as have been defined above:

F) or A)
E) and F) or A) and B)
D), E) and F) or A), B) and C)
C), D), E) and F) or A), B) C) and D)
B), C), D), E) and F) or A), B), C), D) and E)

The chemical nature of the individual steps is already known in principle and they may be employed to the inventive compounds in a similar manner.

Preferred compounds of the formula (IIa) and (IIb) are trans-pinocarveol and myrtenol.

A preferred compound of the formulae (IIIa) and (IIIb) is chlorodiphenylphosphine.

Preferred compounds of the formula (IVa) and (IVb) are:
O-diphenylphosphinyl-trans-pinocarveol and O-diphenylphosphinylmyrtenol.

Preferred compounds of the formula (Va) and (Vb) are:
2-(diphenylphosphinoylmethyl)-6,6-dimethylbicyclo[3.1.1]hept-2-ene and (R)-3-(diphenylphosphinoyl)-6,6-dimethyl-2-methylenebicyclo[3.1.1]heptane. Preferred compounds the formula (VIa) and (VIb) are:
(2S,3R)-2-(diphenylphosphinoylmethyl)-6,6-dimethylbicyclo[3.1.1]heptan-3-ol and (2R,3R)[3-(diphenylphosphinoyl)-6,6-dimethylbicyclo[3.1.1]hept-2-yl]methanol.

Preferred compounds of the formula (VIIa) and (VIIb) are:
(2S,3R)-2-(diphenylphosphinylmethyl)-6,6-dimethylbicyclo[3.1.1]heptan-3-ol and (2R,3R)[3-(diphenylphosphinyl)-6,6-dimethylbicyclo[3.1.1]hept-2-yl]methanol.

Preferred compounds the formula (IXa) and (IXb) are:
(2S,3R)-2-(diphenylphosphinylmethyl)-6,6-dimethyl-3-methanesulphonyloxybicyclo-[3.1.1]heptane and (2R,3R)[3-(diphenylphosphinyl)-6,6-dimethylbicyclo[3.1.1]hept-2-yl]-1-methanesulphonyloxymethane.

A preferred compound of the formulae (Xa) and (Xb) is diphenylphosphine.

In the manner described, the compounds of the formula (I) are obtainable in high yields in an efficient manner.

The invention further embraces transition metal complexes which comprise the inventive compounds of the formula (I).

Transition metal complexes are preferably those of ruthenium, osmium, cobalt, rhodium, iridium, nickel, palladium, platinum and copper, preferably those of ruthenium, rhodium, iridium, nickel, palladium and platinum, more preferably those of ruthenium, rhodium, iridium and palladium.

The inventive transition metal complexes are especially suitable as catalysts. The invention therefore also embraces catalysts which comprise the inventive transition metal complexes.

The catalysts used may, for example, either be isolated transition metal complexes or those transition metal complexes which are obtainable by reacting transition metal compounds and compounds of the formula (I).

Isolated transition metal complexes which contain the compounds of the formula (I) are preferably those in which the ratio of transition metal to compound of the formula (I) is 1:1.

Preference is given to the inventive compounds of the formula (XI)

[(I)L¹₂M][An¹] (XI)

in which (I) represents compounds of the formula (I) with the definition specified there and its areas of preference and
M is rhodium or iridium and
L¹ is in each case a $C_2$-$C_{12}$-alkene, for example ethylene or cyclooctene, or a nitrile, for example acetonitrile, benzonitrile or benzyl nitrile, or
L¹₂ together is a ($C_4$-$C_{12}$)-diene, for example bicyclo[2.1.1]hepta-2,5-diene (norbornadiene) or 1,5-cyclooctadiene and
[An¹] is an anion, preferably methanesulphonate, trifluoromethanesulphonate, tetrafluoroborate, hexafluorophosphate, perchlorate, hexafluoroantimonate, tetra -(bis-3,5-trifluoromethylphenyl)borate or tetraphenylborate.

Preferred transition metal complexes are those which are obtainable by reacting transition metal compounds and compounds of the formula (I).

Suitable transition metal compounds are, for example, those of the formula

M(An²)_q (XIIa)

in which

M is rhodium, iridium, ruthenium, nickel, palladium, platinum or copper and $An^2$ is chloride, bromide, acetate, nitrate, methanesulphonate, trifluoromethanesulphonate or acetylacetonate and q is 3 for rhodium, iridium and ruthenium, is 2 for nickel, palladium and platinum and is 1 for copper, or transition metal complexes of the formula (XIIb)

$$M(An^3)_q L^1{}_2 \qquad (XIIb)$$

in which

M is ruthenium, iridium, ruthenium, nickel, palladium, platinum or copper and $An^3$ is chloride, bromide, acetate, acetylacetonate, methanesulphonate or trifluoromethanesulphonate, tetrafluoroborate or hexafluorophosphate, perchlorate, hexafluoroantimonate, tetra(bis-3,5-trifluoromethylphenyl)borate or tetraphenylborate and q is 1 for rhodium and iridium, is 2 for ruthenium, nickel, palladium and platinum and is 1 for copper, $L^1$ is in each case a $C_2$-$C_{12}$-alkene, for example ethylene or cyclooctene, or a nitrile, for example acetonitrile, benzonitrile or benzyl nitrile, or $L^1{}_2$ together is a ($C_4$-$C_{12}$)-diene, for example bicyclo[2.1.1]hepta-2,5-diene (norbornadiene) or 1,5-cyclooctadiene or transition metal compounds of the formula (XIIc)

$$[ML^2 An^1{}_2]_2 \qquad (XIIc)$$

in which

M is ruthenium and $L^2$ is an aryl radical, for example cymene, mesityl, phenyl or cyclooctadiene, norbornadiene or methylallyl or transition metal compounds of the formula (XIId)

$$Met^3{}_q[M(An^4)_4] \qquad (XIId)$$

in which

M is palladium, nickel, iridium or rhodium and $An^4$ is chloride or bromide and Me is lithium, sodium, potassium, ammonium or organic ammonium and q is 3 for rhodium and iridium, is 2 for nickel, palladium and platinum, or transition metal compounds the formula (XIIe)

$$[M(L^3)_2]An^5 \qquad (XIIe)$$

in which

M is iridium or rhodium and $L^3$ is ($C_4$-$C_{12}$)-diene, for example bicyclo[2.1.1]hepta-2,5-diene (norbornadiene) or 1,5-cyclooctadiene and $An^5$ is a noncoordinating or weakly coordinating anion, for example methanesulphonate, trifluoromethanesulphonate, tetrafluoroborate, hexafluorophosphate, perchlorate, hexafluoroantimonate, tetra(bis-3,5-trifluoromethylphenyl)borate or tetraphenylborate.

Additionally suitable as transition metal compounds are, for example, Ni(1,5-cyclooctadiene)$_2$, Pd$_2$(dibenzylideneacetone)$_3$, Pd[PPh$_3$]$_4$, cyclopentadienyl$_2$Ru, Rh(acac)(CO)$_2$, Ir(pyridine)$_2$(1,5-cyclooctadiene), Cu(phenyl)Br, Cu(phenyl)Cl, Cu(phenyl)I, Cu(PPh$_3$)$_2$Br, [Cu(CH$_3$CN)$_4$]BF$_4$ and [Cu(CH$_3$CN)$_4$]PF$_6$ or polynuclear bridged complexes, for example [Rh(1,5-cyclooctadiene)Cl]$_2$, [Rh(1,5-cyclooctadiene)Br]$_2$, [Rh(ethene)$_2$Cl]$_2$, [Rh(cyclooctene)$_2$Cl]$_2$.

The transition metal compounds used are preferably:

[Rh(cod)(acac)] where acac is acetylacetonate, [Ir(ethylene)$_2$(acac)], [Rh(ethylene)$_2$(acac)], [Rh(cod)Cl]$_2$, [Rh(cod)Br]$_2$, [Rh(cod)$_2$]ClO$_4$, [Rh(cod)$_2$]BF$_4$, [Rh(cod)$_2$]PF$_4$, [Rh(cod)$_2$]ClO$_6$, [Rh(cod)$_2$]OTf, [Rh(cod)$_2$]BAr$_4$ (Ar=3,5-bis-trifluoromethylphenyl), [Rh(cod)$_2$]SbF$_6$, RuCl$_2$(cod), [(cymene)RuCl$_2$]$_2$, [(benzene)RuCl$_2$]$_2$, [(mesityl)RuCl$_2$]$_2$, [(cymene)RuBr$_2$]$_2$, [(cymene)RuI$_2$]$_2$, [(cymene)Ru(BF$_4$)$_2$]$_2$, [(cymene)Ru(PF$_6$)$_2$]$_2$, [(cymene)Ru(BAr$_4$)$_2$]$_2$ (Ar=3,5-bis-trifluoromethylphenyl), [(cymene)Ru(SbF$_6$)$_2$]$_2$, [Ir(cod)Cl]$_2$, [Ir(cod)$_2$]PF$_6$, [Ir(cod)$_2$]ClO$_4$, [Ir(cod)$_2$]SbF$_6$, [Ir(cod)$_2$]BF$_4$, [Ir(cod)$_2$]OTf, [Ir(cod)$_2$]BAr$_4$ (Ar=3,5-bistrifluoromethylphenyl), RuCl$_3$, NiCl$_3$, RhCl$_3$, PdCl$_2$, PdBr$_2$, Pd(OAc)$_2$, Pd$_2$(dibenzylideneacetone)$_3$, Pd(acetylacetonate)$_2$, CuOTf, CuI, CuCl, Cu(OTf)$_2$, CuBr, CuI, CuBr$_2$, CuCl$_2$, CuI$_2$, [Rh(nbd)Cl]$_2$, [Rh(nbd)Br]$_2$, [Rh(nbd)$_2$]ClO$_4$, [Rh(nbd)$_2$]BF$_4$, [Rh(nbd)$_2$]PF$_6$, [Rh(nbd)$_2$]OTf, [Rh(nbd)$_2$]BAr$_4$ (Ar=3,5-bistrifluoromethylphenyl), [Rh(nbd)$_2$]SbF$_6$, RuCl$_2$(nbd), [Ir(nbd)$_2$]PF$_6$, [Ir(nbd)$_2$]ClO$_4$, [Ir(nbd)$_2$]SbF$_6$, [Ir(nbd)$_2$]BF$_4$, [Ir(nbd)$_2$]OTf, [Ir(nbd)$_2$]BAr$_4$ (Ar=3,5-bis-trifluoromethylphenyl), Ir(pyridine)$_2$(nbd), [Ru(DMSO)$_4$Cl$_2$], [Ru(CH$_3$CN)$_4$Cl$_2$], [Ru(PhCN)$_4$Cl$_2$], [Ru(cod)Cl$_2$]$_n$, [Ru(cod)$_4$(methallyl)$_2$], [Ru(acetylacetonate)$_3$].

The amount of the transition metal compounds used may, for example, be 25 to 200 mol % based on the compound of the formula (I) used; preference is given to 50 to 150 mol %, very particular preference to 75 to 125 mol % and even greater preference to 100 to 125 mol %.

The catalysts which comprise the inventive transition metal complexes are especially suitable for use in a process for preparing stereoisomerically enriched, preferably enantiomerically enriched, compounds.

Preference is given to using the catalysts for asymmetric 1,4-additions, asymmetric hydroformylations, asymmetric allylic substitutions, asymmetric hydrocyanations, asymmetric Heck reactions, asymmetric hydroborations and asymmetric hydrogenations, more preferably for asymmetric hydrogenations, asymmetric 1,4-additions, asymmetric hydroborations and asymmetric allylic substitutions.

Preferred asymmetric hydrogenations are, for example, hydrogenations of prochiral C=C bonds, for example of prochiral enamines, enamides, olefins, enol ethers, C=O bonds, for example of prochiral ketones, and C=N bonds, for example of prochiral imines. Particularly preferred asymmetric hydrogenations are hydrogenations of prochiral C=C bonds, for example of prochiral enamines and enamides, olefins.

The invention therefore also embraces a process for preparing stereoisomerically enriched, preferably enantiomerically enriched, compounds by catalytic hydrogenation of olefins, enamines, enamides, imines or ketones, which is characterized in that the catalysts used are those which comprise transition metal complexes of compounds of the formula (I) with the definition specified there.

The amount of the transition metal compound used or of the transition metal complex used may, for example, be 0.001 to 5 mol % based on the substrate used; preference is given to 0.001 to 0.5 mol %, very particular preference to 0.001 to 0.1 mol % and even greater preference to 0.001 to 0.008 mol %.

In a preferred embodiment, asymmetric hydrogenations, 1,4-additions and hydroborations may be carried out, for example, in such a way that the catalyst is generated from a transition metal compound and compound of the formula (I), optionally in a suitable solvent, the substrate is added and the reaction mixture is admixed with the reactant at reaction temperature (hydrogen, boronic acids, boranes, etc.).

Suitable solvents for the asymmetric catalysis are, for example, chlorinated alkanes such as methyl chloride, short-chain $C_1$-$C_6$-alcohols, for example methanol, isopropanol or ethanol, aromatic hydrocarbons, for example toluene or benzene, ketones, for example acetone, or carboxylic esters, for example ethyl acetate.

The asymmetric catalysis is carried out advantageously at a temperature of −20° C. to 200° C., preferably 0 to 100° C. and more preferably at 20° to 70° C.

The inventive catalysts are suitable in a process for preparing stereoisomerically enriched, preferably enantiomerically enriched, active ingredients in medicaments and agrochemicals, or intermediates of these two classes.

The advantage of the present invention is that the compounds of the formula (I) can be prepared in an efficient manner and their electronic and steric properties are variable to a wide degree starting from readily available reactants. In addition, the inventive ligands and their transition metal complexes exhibit good performance in asymmetric syntheses.

EXAMPLES

General Remarks:

All reactions with air- or moisture-sensitive compounds were carried out under an argon atmosphere using Schlenk technology. The solvents were dried over suitable reagents and distilled under a nitrogen atmosphere. In some cases, the solvents were distilled beforehand on a rotary evaporator. Commercially available reagents were, unless stated specifically, used without further purification. The silica gel mentioned in the text is silica gel 60 (Merck 0.04-0.063 mm, 230-400 mesh), alumina is aluminium oxide (Fluka, treated with water to attain Brockmann grade III), celite is kieselguhr (Merck). The oil-pump vacuum corresponds to about 0.2 mbar. The reaction temperatures relate to internal temperatures.

General procedure 1 for the conversion of phosphine oxides to the corresponding phosphine-borane complexes.

Under an argon atmosphere, 20 ml of anhydrous toluene, 2 ml of polymethylhydrosiloxane (Aldrich) and 1.5 ml of titanium isopropoxide (Acros) were introduced into a dried Schlenk flask. A sample of the reaction mixture was introduced into an NMR tube in order to monitor the reaction. The reduction mixture and the tube were heated at 105° C. for 2-4 h until complete reduction was detected in the $^{31}$P NMR (oxide at 30-40 ppm, phosphines at −20-0 ppm). The reaction mixture is allowed to cool and 1 ml of borane-dimethyl sulphide complex (Aldrich) is added. After a few minutes, the mixture is introduced into a 250 ml Erlenmeyer flask with 5 ml of methanol (hydrogen evolution!). After the gas evolution has abated, the solution is introduced into a Nalgene® bottle with 20 ml of 48% HF and 20 ml of water and stirred at room temperature for 12 h. (This removes the PMHS excess which is otherwise difficult to remove.) The organic phase is removed and the aqueous phase extracted with 15 ml of toluene. The combined organic phases are washed with saturated sodium hydrogencarbonate solution and brine, and dried over magnesium sulphate, and the solvent is removed under reduced pressure. The residue is dissolved in a small amount of diethyl ether and filtered through a 3 cm silica gel layer, the latter is washed with diethyl ether, the solvent is removed and the substance is dried under reduced pressure in order to obtain the phosphine-borane complex as a viscous oil which gradually solidifies. Typical yield range 95-99%.

General procedure 2 for the conversion of phosphine-borane alcohols to the corresponding mesylates and nucleophilic substitution with diphenylphosphine.

Under an argon atmosphere, 5 mM of a phosphine-borane alcohol and 40 ml of dry dichloromethane were introduced into a 100 ml dry Schlenk vessel. The mixture was cooled to −30° C. and 2.4 ml of anhydrous triethylamine were added.

1.2 ml of methanesulphonyl chloride were then added dropwise at this temperature with vigorous stirring. The reaction mixture was left at −30° for 2 h and introduced into 200 ml of anhydrous diethyl ether with stirring at this temperature. After 5 min, the white precipitate was filtered off through a 3 cm silica gel layer. The filtercake was washed with 100 ml diethyl ether and the solvent was removed under reduced pressure down to a residue of 10 ml. The remaining solvent was removed under high vacuum in order to prevent thermal stress. The remaining residue was left under high vacuum for 5 h in order to remove traces of MsCl. The thus obtained mesylate was used in the next step without further purification.

In a 100 ml Schlenk vessel under an argon atmosphere, 2.00 g of t-BuOK in 25 ml of anhydrous THF and 2.32 g (3 equivalents) of diphenylphosphine (Strem) were added. The orange-coloured solution was cooled to −20° C. and the above-described mesylate was introduced slowly in 10 ml of THF. The reaction mixture was allowed to warm to room temperature and then heated to 50° C. for 18 h. After cooling to room temperature, 2.5 ml of borane-dimethyl sulphide complex (Aldrich) were added. The contents of the reaction vessel were introduced cautiously into a 250 ml Erlenmeyer flask with 10 ml of methanol. After the gas evolution had abated, 50 ml of saturated $NH_4Cl$ solution were added, the organic phase was removed and the aqueous phase was extracted twice with 20 ml each time of dichloromethane. The combined organic phases were washed with saturated sodium chloride solution and dried over magnesium sulphate, and the solvent was removed under reduced pressure. The residue was dissolved in 5 ml of dichloromethane-pentane (1:1) and filtered through a 5 cm alumina layer on a 25 mm (diameter) filter. The majority of the solvent was removed under reduced pressure and the residue was diluted with 15 ml of diethyl ether and left at 0° C. for 12 h. The solid formed was filtered off and dried under reduced pressure.

General procedure 3 for the deprotection of a phosphine-borane with N,N'-bis-(3-aminopropyl)piperazine.

Phosphine-borane (1 mM) was introduced under an argon atmosphere into a 10 ml Schlenk vessel and dissolved in 2 ml of anhydrous toluene. 1 ml of N,N'-bis(3-aminopropyl)piperazine (Lancaster) was added to this solution. The reaction mixture was heated to 105° C. for 2 h, cooled to room temperature and diluted with 10 ml of diethyl ether. Under an argon atmosphere, the mixture was filtered through diethyl ether-moistened silica gel into a flask (very strict oxygen exclusion). The silica gel was rewashed twice with 30 ml each time of diethyl ether. The solvent was removed under reduced pressure. The resulting phosphine is obtained as a white foam or highly viscous oil which solidifies. The product was stored under an argon atmosphere.

General procedure 4 for the hydrogenation of a phosphine oxide over Raney nickel.

6.0 g of Raney nickel (50% water-moist, Acros) was washed by mixing and decanting off three times with 20 ml units of methanol, admixed with 30 ml of methanol and transferred into a 200 ml V4A autoclave. 8 mM of diphenylphosphine oxide were added and the autoclave was charged with hydrogen until 50 bar were attained. The hydrogenation was effected at 50° C. over a period of 48 h, the autoclave was decompressed and the mixture was filtered through a Celite layer. The residue was washed with methanol. The solvent of the filtrate was removed under reduced pressure and the product was obtained in virtually quantitative yield as a colourless foam.

Example 1

Preparation of ((2S,3S)-3-diphenylphosphinyl-2-[(diphenylphosphinyl)methyl]-6,6-dimethylbicyclo[3.1.1]heptane

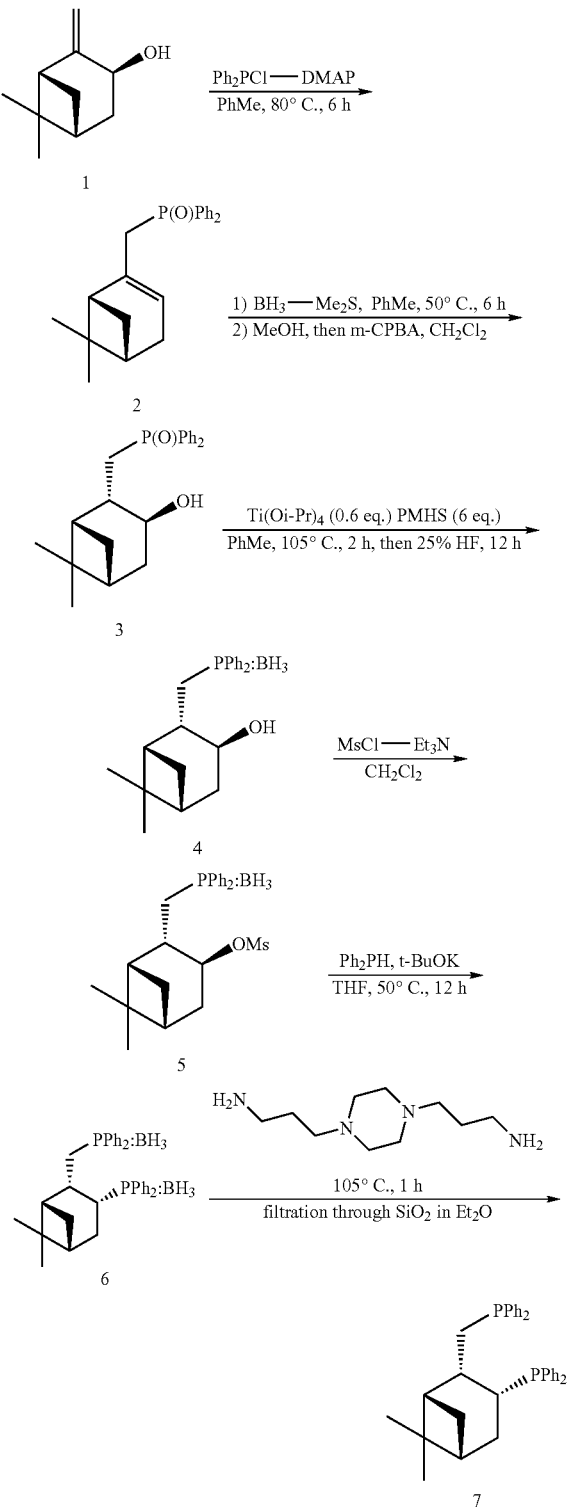

1a) (2S,3R)-2-(Diphenylphosphinoylmethyl)-6,6-dimethylbicyclo[3.1.1]heptan-3-ol(3)

Trans-pinocarveol was obtained as described in *Organic Syntheses, Coll. Vol. VI*, p. 947.

10.2 g (84 mmol) of 4-dimethylaminopyridine (Acros) were introduced into a 250 ml Schlenk flask and dissolved in 100 ml of anhydrous toluene under an argon atmosphere. Trans-pinocarveol (12.7 g, 84 mmol) was added, the reaction mixture was cooled to −30° C. and 15.2 ml (84 mmol) of diphenylchlorophosphine (Strem, 98%, distilled under reduced pressure before use) were added dropwise at this temperature over 5 min. The reaction mixture was warmed to room temperature and then heated at 80° C. for 6 h. $^{31}$P NMR showed full rearrangement (diphenyl phosphinite 126 ppm, diphenylphosphine oxide 29 ppm). The reaction mixture was hot-filtered through a Celite layer and the filter cake was washed with toluene. The filtrate was concentrated to approx. 70 ml and then 2 ml (120 mmol) of borane-dimethyl sulphide complex (Aldrich) were added cautiously. The reaction mixture was heated to 50° C. for 6 h and cooled, and the contents were introduced cautiously into a 1 l Erlenmeyer flask with 70 ml of methanol. After 4 h, the solution was concentrated under reduced pressure and the residue was taken up in 80 ml of dichloromethane.

25 g of meta-chloroperbenzoic acid (70-75%, Acros) were dissolved in 200 ml of dichloromethane, and the solution was dried over magnesium sulphate and introduced into a 500 ml two-necked flask with dropping funnel and thermometer. The flask was suspended in a cooling mixture of acetone and dry ice and the solution of the hydroborated phosphine oxide was added dropwise such that the temperature did not rise above 15° C. On completion of addition, the reaction mixture was stirred for another 1 h and then filtered. The filtrate was stirred with a solution of 80 g of $Na_2S_2O_5$ in 200 ml of $H_2O$ for 10 min, the phases were separated and the organic phase was washed twice with 100 ml each time of 2M NaOH and brine, and dried over magnesium sulphate, and the solvent was removed under reduced pressure. The waxlike residue was stirred in 200 ml of diethyl ether for 24 h, and the precipitate formed was filtered off, washed with diethyl ether and dried under reduced pressure.

Yield: 18.4 g (62%).

$^1$H NMR: 7.71-7.63 (m, 4H), 7.50-7.36 (m, 6H), 5.56 (bs, 1H), 4.34-4.24 (m, 1H), 3.64 (bs, 1H), 2.56-2.38 (m, 2H), 2.29-2.13 (m, 2H), 1.94-1.86 (m, 1H), 1.14 (s, 3H), 0.99 (s, 1H), 0.96 (s, 1H), 0.91 (s, 3H).

$^{13}$C NMR: 134.6, 133.2, 132.7, 132.4-132.3 (m), 131.5 (d, J=9.2 Hz), 130.8 (d, J=9.2 Hz), 129.3 (m), 129.1 (m), 70.2, 51.3 (d, J=14.4 Hz), 48.3, 41.8, 38.7, 38.0 (d, J=69 Hz), 37.0, 34.5, 27.9, 24.2.

$^{31}$P: 36.0

HRMS: 355.1809 ($C_{22}H_{28}O_2P$, [M]$^+$)

Mp: 200-200.5° C.

1b) (2S,3R)-2-(Diphenylphosphinylmethyl)-6,6-dimethylbicyclo[3.1.1]heptan-3-ol -borane complex (4)

According to the general procedure 2.1, the compound 3 was converted to the corresponding phosphine-borane 4. Colourless, waxlike substance which crystallizes during storage, yield: 96%.

$^1$H NMR: 7.78-7.62 (m, 4H), 7.56-7.40 (m, 6H), 4.20-4.10 (bs, 1H), 2.70-2.40 (m, 1H), 2.48 (bs, 1H), 2.33-2.20 (m, 2H), 1.93 (s, 1H), 1.86 (s, 1H), 1.79 (s, 1H), 1.75 (s, 1H), 1.17 (s, 3H), 1.15 (s, 1H), 1.11 (s, 1H), 0.96 (s, 3H).

$^{13}$C NMR: 132.8 (d, J=8.8 Hz), 132.3 (d, J=8.8 Hz), 131.8, 131.6, 131.1, 129.3 (d, J=4.7 Hz), 129.2 (d, J=4.7 Hz), 128.8, 71.1 (d, J=5.6 Hz), 48.5, 48.4, 41.1, 38.1, 33.8, 33.3, 32.5, 27.4, 24.1.

$^{31}$P: 15.4 (bs)

HRMS: 351.2051 ($C_{22}H_{29}BOP$, [M–H]$^+$)

Mp: 107-107.5° C.

1c) (2S,3S)-3-Diphenylphosphinyl-2-[(diphenylphosphinyl)methyl]-6,6-dimethylbicyclo[3.1.1]heptane bis-borane complex (6).

The compound 4 was converted to the corresponding phosphine-borane 6 by the general procedure 2.2. The residue obtained after the removal of the solvent was dissolved rapidly in 25 ml of diethyl ether. After a few minutes, the crystallization of the product begins. After 12 h, the crystals are filtered off, washed with a small amount of diethyl ether and dried under reduced pressure. Colourless crystals, yield: 55%.

$^1$H NMR: 7.93-7.79 (m, 2H), 7.71-7.50 (m, 4H), 7.47-7.21 (m, 8H), 7.22-7.00 (m, 4H), 6.90-6.77 (m, 2H), 3.70-3.45 (m, 1H), 3.26 (bs, 1H), 3.10-2.85 (m, 1H), 2.16-1.90 (m, 1H), 1.80-0.73 (m, 6H), 0.91 (s, 3H), 0.87 (s, 3H).

$^{13}$C NMR: 131.5, 131.4, 131.2, 131.1, 130.7, 130.4, 130.2, 130.0 (d, J=8.8 Hz), 129.8, 129.6 (m) 129.4, 129.3, 129.3, 129.2, 129.0, 128.8, 128.5 (d, J=9.4 Hz), 128.1, 127.6 (d, J=10.0 Hz), 127.3 (d, J=10.0 Hz), 44.5, 38.9, 37.2, 33.9, 32.7, 28.1, 27.2 (d, J=10.6 Hz), 26.8 (d, J=10.6 Hz), 25.6 (d, J=8.5 Hz), 19.9.

$^{31}$P: 17.5 (bs), 19.0 (bs).

HRMS: 534.2953 ($C_{34}H_{42}B_2P_2$, [M]$^+$)

Mp: 195-196° C.

1d) (2S,3S)-3-Diphenylphosphinyl-2-[(diphenylphosphinyl)methyl]-6,6-dimethylbicyclo[3.1.1]heptane (7).

The compound 6 was converted to the corresponding phosphine 7 according to the general procedure 2.3. Yield 95%, colourless, very viscous oil which crystallizes slowly during storage.

$^1$H NMR: 7.49-7.36 (m, 4H), 7.25-7.00 (m, 16H), 6.85-6.78 (m, 2H), 3.24-3.10 (m, 1H), 2.53-2.37 (m, 3H), 2.36-2.32 (m, 1H), 2.10-2.00 (m, 1H), 1.76 (bs, 1H), 1.58-1.40 (m, 2H), 1.27 (d, J=10.1 Hz, 1H), 1.10 (s, 3H), 0.91 (s, 3H).

$^{13}$C NMR: 139.3 (d, J=14.1 Hz), 138.2 (d, J=11.8 Hz), 137.4 (d, J=13.5 Hz), 137.0 (d, J=14.7 Hz) 133.4 (d, J=20.8 Hz), 132.1 (d, J=19.4 Hz) 131.4 (d, J=18.5 Hz) 127.9-127.0 (m), 124.3, 45.3 (d, J=14.4 Hz), 40.1, 37.2, 35.1-34.8 (m), 31.7 (d, J=17.0 Hz), 29.8-29.3 (m), 27.2-27.0 (m), 26.6, 26.1, 20.0.

$^{31}$P: –15.6 (d, J=3.4 Hz), –16.2 (d, J=3.4 Hz).

HRMS: 506.2288 ($C_{34}H_{36}P_2$, [M]$^+$)

Example 2

Synthesis of (2R,3R)-2-diphenylphosphinyl-3-[(diphenylphosphinyl)methyl]bicyclo-[3.1.1]heptane

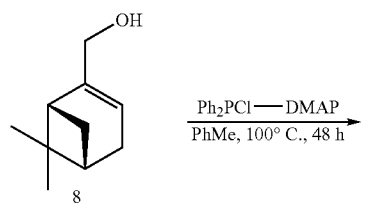

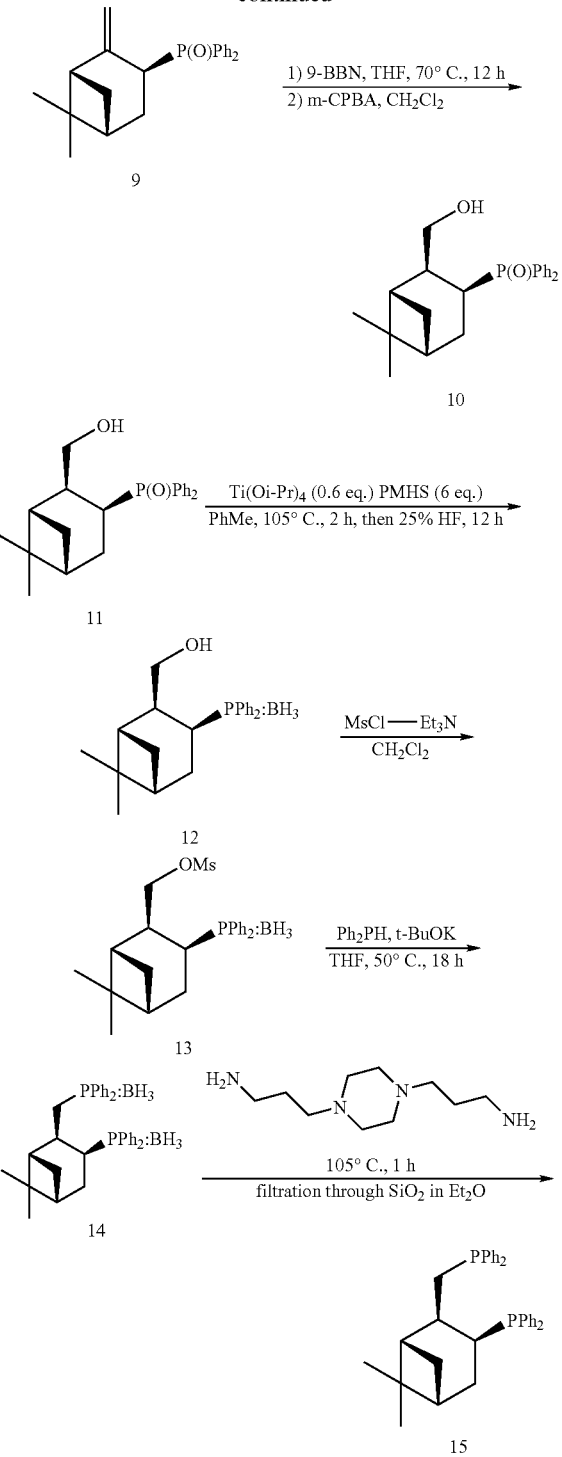

1a) (R)-3-(Diphenylphosphinoyl)-6,6-dimethyl-2-methylenebicyclo[3.1.1]heptane (9)

Under an argon atmosphere, 7.60 g (62 mmol) of 4-dimethylaminopyridine (Acros) in 120 ml of toluene were introduced into a 250 ml Schlenk flask. 9.50 g (62 mmol) of (–)-myrtenol (Dragoco, >99% ee) were added and the solution was cooled to –30° C. At this temperature, 11.2 ml (62 mmol) of diphenylchlorophosphine (Strem, 98%, distilled in vacuo before use) were added dropwise over 5 min. The reaction mixture was warmed to room temperature and then heated to 100° C. for 48 h. The suspension was hot-filtered through Celite and the precipitate washed with 50 ml of hot toluene. The solvent of the filtrate was removed under reduced pressure, and the residue was filtered off and washed with diethyl ether. 20.8 g (90%) of white powder were obtained.

$^1$H NMR: 7.88-7.82 (m, 4H), 7.50-7.43 (m, 6H), 4.56 (d, J=3.4 Hz, 1H), 3.91 (s, 1H), 3.64 (bs, 1H), 2.41-1.94 (m, 6H), 1.24 (s, 3H), 0.77 (s, 3H).

$^{13}$C NMR: 145.4 (d, J=8.5 Hz), 134.5 (d, J=10.0 Hz), 133.2 (d, J=13.2 Hz), 132.2 (d, J=8.5 Hz), 131.7 (m), 131.5 (d, J=8.5 Hz), 129.1 (d, J=11.2 Hz), 128.6 (d, J=11.2 Hz), 112.3 (d, J=7.6 Hz), 52.0, 41.0, 39.9, 34.9 (d, J=67 Hz), 26.9, 26.5, 26.1, 21.7.

$^{31}$P: 37.0

HRMS: 336.1647 ($C_{22}H_{25}OP$)

Mp: 189.5-190° C.

2b) (2R,3R)[3-(Diphenylphosphinoyl)-6,6-dimethyl-bicyclo[3.1.1]hept-2-yl]-methanol (10)

8.0 g (20 mmol) of phosphine oxide (9) were dissolved under an argon atmosphere in 50 ml of 0.5 M THF solution of 9-BBN (Aldrich) and the reaction mixture was heated to 70° C. in a closed reaction vessel for 12 h.

A solution of 25 g of meta-chloroperbenzoic acid (70-75%, Acros) in 250 ml of dichloromethane, which had been dried over $MgSO_4$, was introduced into a 500 ml three-necked flask. The flask was cooled to 15° C. in an acetone-dry ice bath and a solution of hydroborated phosphine oxide was added in such a way that the temperature did not rise above 20° C. On completion of addition, the reaction mixture was stirred for 1 h and then filtered. The filtrate was stirred with a solution of 80 g of $Na_2S_2O_5$ in 200 ml of $H_2O$ for 10 min, the phases were separated and the organic phase was washed twice with 100 ml each time of 2M NaOH, and brine, and dried over magnesium sulphate, and the solvent was removed in vacuo. The waxlike residue was extracted by stirring with 100 ml of diethyl ether for 24 h, and the precipitate formed was filtered off, washed with diethyl ether and concentrated under reduced pressure. Yield 5.65 g (67%), white powder.

$^1$H NMR: 7.94-7.82 (m, 2H), 7.80-7.67 (m, 2H), 7.50-7.23 (m, 6H), 4.81 (bs, 1H), 3.83 (bs, 1H), 3.52-3.25 (m, 2H), 2.58 (bs, 1H), 2.27 (bs, 1H), 2.12-1.90 (m, 2H), 1.87-1.65 (m, 3H), 1.19 (s, 3H), 0.98 (s, 3H).

$^{13}$C NMR: 135.9, 134.6, 134.2, 132.9, 132.0, 131.7, 131.1 (d, J=8.7 Hz), 130.4 (d, J=8.7 Hz), 129.5 (d, J=11.0 Hz), 129.1 (d, J=11.0 Hz), 89.0, 65.4 (d, J=12.0 Hz), 46.1, 41.5 (d, J=3.8 Hz), 40.0 (d, J=5.0 Hz), 39.5, 29.4, 29.0, 28.7, 28.5, 27.0, 21.3.

$^{31}$P: 39.1

HRMS: 335.1825 ($C_{22}H_{28}OP$)

Mp: 185.5-186° C.

2c) (2R,3R)-[3-(Diphenylphosphinyl)-6,6-dimethyl-bicyclo[3.1.1]hept-2-yl]-methanol-borane complex (12)

The compound 10 was converted to the corresponding phosphine-borane complex 12 by the general procedure 2.1. Yield 95%, colourless, very viscous oil.

$^1$H NMR: 7.82-7.72 (m, 2H), 7.61-7.52 (m, 2H), 7.41-7.32 (m, 3H), 7.27-7.18 (m, 3H), 3.55-3.35 (m, 2H), 2.61 (bs, 1H), 2.17-2.00 (m, 2H), 1.94-1.77 (m, 2H), 1.43-0.99 (m, 4H), 1.12 (s, 3H), 0.95 (s, 3H).

$^{13}$C NMR: 132.8 (d, J=8.8 Hz), 132.3 (d, J=8.8 Hz), 131.8, 131.6, 131.1, 129.3 (d, J=4.7 Hz), 129.2 (d, J=4.7 Hz), 128.8, 71.1 (d, J=5.6 Hz), 48.5, 48.4, 41.1, 38.1, 33.8, 33.3, 32.5, 27.4, 24.1.

$^{31}$P: 21.0 (bs)

HRMS: 351.2047 ($C_{22}H_{29}BOP$, [M–H]$^+$)

2d) (2R,3R)-3-Diphenylphosphinyl-2-[(diphenylphosphinyl)methyl]-6,6-dimethylbicyclo[3.1.1] heptane bis-borane complex (14).

The compound 12 was converted to the corresponding phosphine-borane 14 by the general procedure 2.2. After the solvent had been removed on a rotary evaporator, the residue was dissolved rapidly in 25 ml of diethyl ether. After a few minutes, the crystallization of the product begins. After 12 h, the crystals were filtered off, washed with a small amount of diethyl ether and dried under reduced pressure. Yield 48%, colourless crystals:

$^1$H NMR: 7.90-7.80 (m, 2H), 7.62-7.53 (m, 2H), 7.52-7.44 (m, 2H), 7.33-7.09 (m, 10H), 7.10-6.98 (m, 2H), 6.86-6.73 (m, 2H), 3.58-3.35 (m, 1H), 3.13-2.81 (m, 2H), 2.25-2.00 (m, 1H), 1.99-1.86 (m, 1H), 1.77 (bs, 1H), 1.64 (bs, 1H), 1.20 (d, J=10.3 Hz), 1.09 (s, 1H), 0.87 (s, 3H), 0.71 (s, 1H), 0.50 (s, 3H).

$^{13}$C NMR: 133.5 (d, J=9.4 Hz), 133.0, 132.9, 132.8, 132.7, 132.1, 131.8, 131.7, 131.6, 131.3, 131.0, 130.9-130.7 (m), 130.2 (d, J=10.3 Hz), 129.9 (d, J=9.7 Hz), 129.5, 129.1, 129.0, 128.2, 44.2, 40.7 (d, J=8.5 Hz), 39.1, 37.4, 29.0, 28.5, 27.9, 27.5, 27.2, 23.0.

$^{31}$P: 17.4 (bs), 19.0 (bs)

HRMS: 534.2926 ($C_{34}H_{42}B_2P_2$, [M]$^+$)

Mp: 195.5-196° C.

2e) (2R,3R)-3-Diphenylphosphinyl-2-[(diphenylphosphinyl)methyl]-6,6-dimethylbicyclo[3.1.1] heptane (15).

The compound 14 was converted to the corresponding phosphine 15 according to the general procedure 2.3. Heating time: 2 h. Yield 96%, colourless, very viscous mass, solidifies slowly in the course of storage.

$^1$H NMR: 7.55-7.47 (m, 2H), 7.45-7.35 (m, 2H), 7.33-7.23 (m, 2H), 7.22-7.10 (m, 10H), 7.10-7.00 (m, 2H), 6.84-6.74 (m, 2H), 3.22 (t, J=9.1 Hz, 1H), 2.65 (t, J=13.1 Hz, 1H), 2.54-2.40 (m, 2H), 2.32-2.21 (m, 1H), 2.14-2.03 (m, 1H), 1.82-1.71 (m, 1H), 1.69-1.58 (m, 1H), 1.28 (d, J=9.8 Hz, 1H), 1.08 (s, 3H), 1.04 (s, 3H), $^{13}$C NMR: 138.8 (d, J=12.9 Hz), 137.9 (d, J=12.6 Hz), 137.1 (d, J=13.5 Hz), 136.7 (d, J=14.7 Hz), 133.3 (d, J=20.8 Hz), 132.1, 131.8, 131.6, 128.1-126.7 (m), 43.6 (d, J=13.5 Hz), 40.1, 38.6-38.3 (m), 38.2, 30.3-29.2 (m), 27.1-26.6 (m), 26.6 (d, J=31.7 Hz), 22.2.

$^{31}$P: –15.7 (d, J=3.2 Hz), –16.3 (d, J=3.2 Hz)

HRMS: 506.2288 ($C_{34}H_{36}P_2$, [M]$^+$)

Example 3

(2S,3S)-2-[(Dicyclohexylphosphinyl)methyl]-3-diphenylphosphinyl-6,6-dimethylbicyclo[3.1.1]heptane

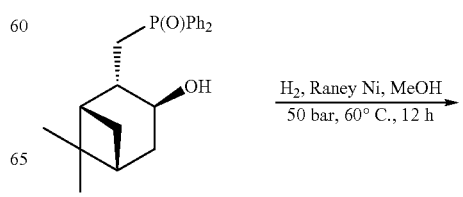

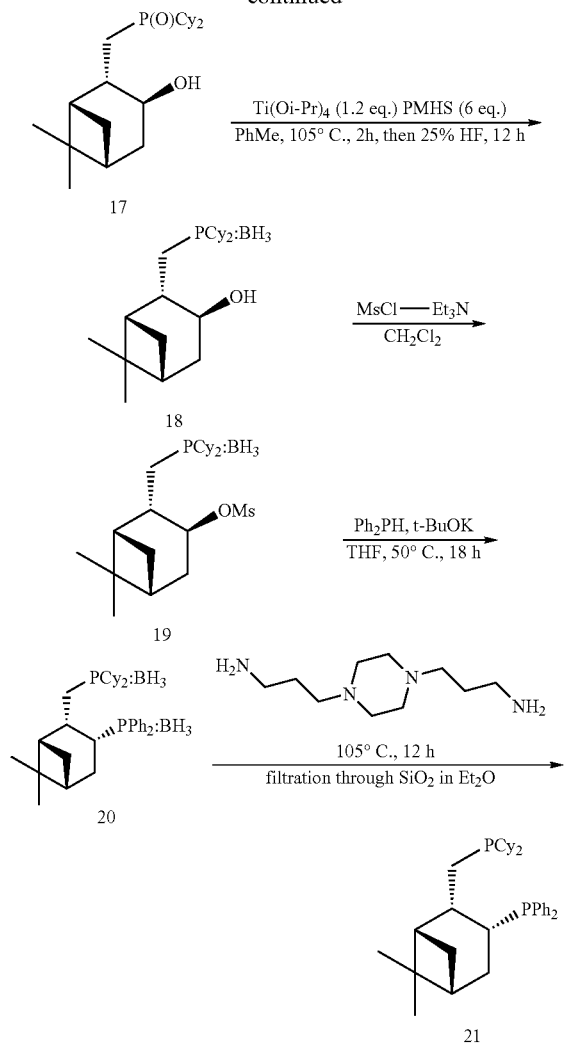

3a) (2S,3R)-[3-(Dicyclohexylphosphinoyl)-6,6-dimethylbicyclo[3.1.1]hept-2-yl]-methanol (17)

According to the general procedure 2.4, the compound 3 was converted to the adduct 17. Yield 97%, colourless solid.

$^1$H NMR: 5.94 (s, 1H), 4.05 (bs, 1H), 2.49-2.19 (m, 3H), 2.08-1.54 (m, 17H), 1.52-1.06 (m, 14H), 1.16 (s, 3H), 0.90 (s, 3H).

$^{13}$C NMR: 70.9, 51.0, 50.2, 42.9, 39.8, 38.7, 38.1, 37.7 (d, J=14.7 Hz), 36.8, 35.2, 31.7 (d, J=57.5 Hz), 28.9, 28.3-26.7 (m), 26.3, 25.3.

$^{31}$P: 61.0

HRMS: 367.2728 ($C_{22}H_{40}PO_2$, [M+H]$^+$)

Mp: 160-161° C.

3b) (2R,3R)[3-(Dicyclohexylphosphinoyl)-6,6-dimethylbicyclo[3.1.1]hept-2-yl]-methanol-borane complex (18)

The compound 17 was converted to the corresponding phosphine-borane complex 18 according to the general procedure 2.1. Yield 93%, colourless solid.

$^1$H NMR: 4.01-3.92 (m, 1H), 2.50-2.08 (m, 4H), 1.97-1.47 (m, 19H), 1.42-1.05 (m, 18H), 0.84 (s, 3H).

$^{13}$C NMR: 69.4, 47.7, 47.4, 39.7, 36.5 (d, J=24.3 Hz), 32.1-30.3 (m), 26.6-24.3 (m), 22.8.

$^{31}$P: 34 (bs)

HRMS: 363.2978 ($C_{22}H_{41}BOP$, [M−H]$^+$)

Mp: 103-104° C.

3c) (2R,3R)-3-Dicyclohexylphosphinyl-2-[(diphenylphosphinyl)methyl]-6,6-dimethylbicyclo[3.1.1]heptane-bisborane complex (20).

The compound 18 was converted to the corresponding phosphine-borane 20 according to the general procedure 2.2. The residue obtained after the removal of the solvent was dissolved rapidly in 25 ml of diethyl ether. After a few minutes, the crystallization of the product begins. After 12 h, the crystals are filtered off, washed with a small amount of diethyl ether and dried under reduced pressure. Yield 44%, colourless crystals.

$^1$H NMR: 7.79-7.69 (m, 4H), 7.48-7.37 (m, 6H), 3.29-3.00 (m, 3H), 2.60-2.45 (m, 1H), 2.28-2.08 (m, 2H), 2.07-1.79 (m, 8H), 1.78-1.56 (m, 6H), 1.55-1.05 (m, 18H), 1.02 (s, 3H), 1.00 (s, 3H).

$^{13}$C NMR: 132.5 (d, J=9.4 Hz), 132.2, 132.0 (d, J=8.8 Hz), 131.5, 131.2, 131.0, 130.3, 129.1 (d, J=10.0 Hz), 128.9 (d, J=10.0 Hz), 46.9, 40.8, 38.4, 35.9, 34.6 (d, J=30.8 Hz), 33.9 (d, J=27.8 Hz), 30.2, 29.7, 29.4, 29.2, 28.8, 28.4-27.5 (m), 26.4 (d, J=22.0 Hz), 24.6-24.0 (m), 21.5.

$^{31}$P: 16.0 (bs), 33.5 (bs).

HRMS: 531.3499($C_{34}H_{50}BP_2$, [M−BH$_4$]$^+$)

Mp: 228-229° C.

3d) (2R,3R)-3-Diphenylphosphinyl-2-[(diphenylphosphinyl)methyl]-6,6-dimethylbicyclo[3.1.1]heptane (21).

The compound 20 was converted to the corresponding phosphine 21 according to the general procedure 2.3. Reaction time: 12 h. Yield 96%, colourless, very viscous oil.

$^1$H NMR: 7.42-7.32 (m, 4H), 7.26-7.17 (m, 6H), 2.73-2.60 (m, 3H), 2.49-2.20 (m, 7H), 2.07-1.37 (m, 16H), 1.29-0.98 (m, 15H), 0.94 (s, 3H).

$^{13}$C NMR: 138.4 (d, J=11.5 Hz), 137.8 (d, J=14.1 Hz), 132.4 (d, J=19.1 Hz), 131.8 (d, J=18.2 Hz), 127.5, 127.4-126.8 (m), 55.5, 52.4, 46.3, 40.4, 39.9, 37.2, 36.4, 32.7-30.3 (m), 29.6, 29.3, 28.2, 27.7, 27.4-26.3 (m), 25.5 (d, J=23.8 Hz), 24.4-23.7 (m), 20.3.

$^{31}$P: −3.8 (s), −17.5 (s).

Example 4

Synthesis of (2R,3R)-3-dicyclohexylphosphinyl-2-[(diphenylphosphinyl)methyl]-6,6-dimethylbicyclo[3.1.1]heptane

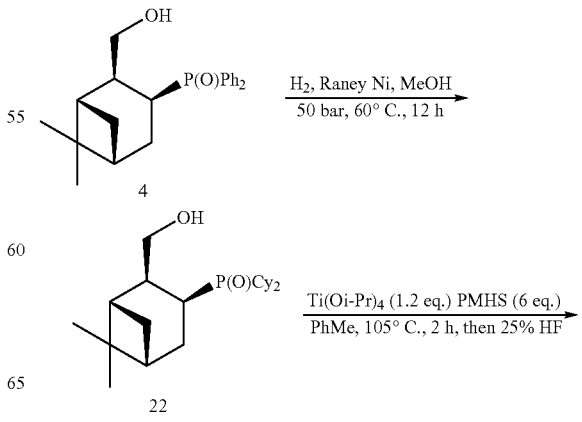

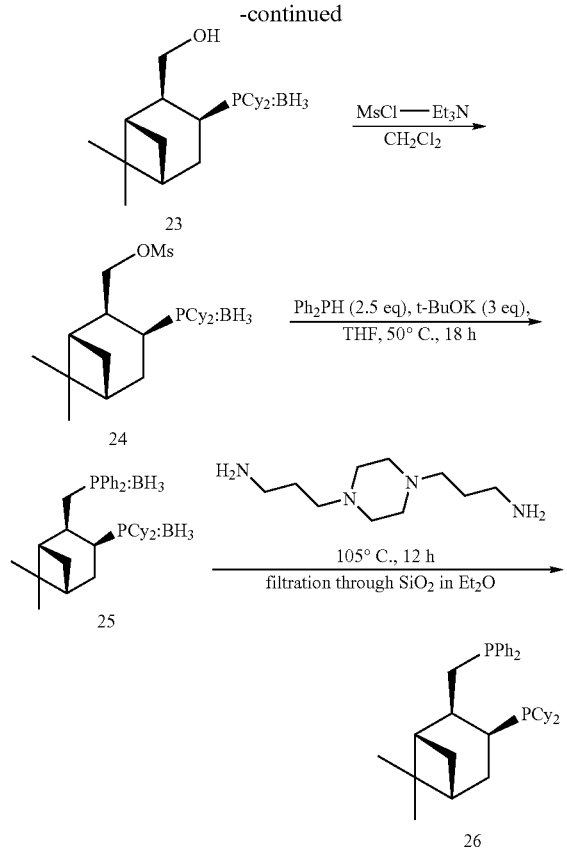

Example 5

(2R,3R)[3-(Dicyclohexylphosphinoyl)-6,6-dimethyl-bicyclo[3.1.1]hept-2-yl]methanol (22)

According to the general procedure 2.4, the compound 4 was converted to the adduct 22. Yield 98%, white foam.

$^1$H NMR: 6.05 (bs, 1H), 3.92 (bs, 1H), 3.66-3.48 (m, 1H), 3.00-2.78 (m, 1H), 2.59 (bs, 1H), 2.31-1.05 (m, 36H), 0.94 (s, 3H).

$^{13}$C NMR: 65.8, 46.3, 42.7, 39.7, 39.1, 37.8, 37.0, 35.6, 34.8, 28.3, 27.3, 27.2-24.9 (m), 20.5.

$^{31}$P: 62.0.

HRMS: 367.2767 ($C_{22}H_{40}PO_2$, [M+H]$^+$)

6.2. (2R,3R)[3-(Dicyclohexyl)-6,6-dimethylbicyclo[3.1.1]hept-2-yl]methanol-borane complex (12)

The compound 22 was converted to the corresponding phosphine-borane complex 23 according to the general procedure 2.1. Yield 94%, colourless, very viscous oil.

$^1$H NMR: 4.01-3.92 (m, 1H), 3.80-3.70 (m, 1H), 3.00-2.80 (m, 1H), 2.55-2.37 (m, 1H), 2.31-1.06 (m, 33H), 1.01 (s, 3H).

$^{13}$C NMR: 63.3, 49.3, 43.5, 41.3, 40.0, 37.1, 33.2, 32.8, 32.4, 28.8, 28.0, 27.7, 27.2-27.0 (m), 25.2, 21.3, 21.0, 20.4.

$^{31}$P: 17.2 (bs)

HRMS: 363.3014 ($C_{22}H_{41}$BOP, [M−H]$^+$)

5c) (2R,3R)-3-Dicyclohexyl-2-[(diphenylphosphinyl)methyl]-6,6-dimethylbicyclo[3.1.1]heptane-bisborane complex (25).

The compound 23 was converted to the corresponding bisphosphine-borane 25 according to the general procedure 2.2. The residue obtained after the removal of the solvent was dissolved in 10 ml of dichloromethane. 50 ml of methanol were added and the solution was concentrated to half its volume on a rotary evaporator. The suspension was stored in a refrigerator at 0° C. After 12 h, the crystals formed were filtered off, washed with a small amount of diethyl ether and dried under reduced pressure. Yield 48%, colourless crystals.

$^1$H NMR: 7.98-7.88 (m, 2H), 7.68-7.58 (m, 2H), 7.51-7.42 (m, 3H), 7.35-7.23 (m, 3H), 3.68-3.42 (m, 1H), 3.09-2.91 (m, 1H), 2.43-2.14 (m, 4H), 1.91-0.57 (m, 31H), 0.53-0.29 (m, 1H).

$^{13}$C NMR: 132.7 (d, J=8.3 Hz), 131.9, 131.2, 131.1, 130.4, 129.9 (d, J=9.6 Hz), 129.7, 129.0, 129.0 (d, J=9.6 Hz), 44.8, 41.0, 39.3, 37.4, 34.7 (d, J=32.0 Hz), 32.7 (d, J=32.0 Hz), 28.2-25.8 (m), 23.4, 22.0-21.3 (m).

$^{31}$P: 16.8 (bs), 28.7 (bs).

HRMS: 531.3467($C_{34}H_{50}BP_2$, [M−BH$_4$]$^+$).

Mp: 228-9° C.

5d) (2R,3R)-3-Diphenylphosphinyl-2-[(diphenylphosphinyl)methyl]-6,6-dimethylbicyclo[3.1.1]heptane (26).

The compound 25 was converted to the corresponding phosphine 26 according to the general procedure 2.3. Reaction time: 12 h. Yield 95%, colourless, very viscous product.

$^1$H NMR: 7.64-7.52 (m, 2H), 7.47-7.35 (m, 2H), 7.35-7.21 (m, 3H), 7.20-7.10 (m, 3H), 3.40-3.20 (m, 1H), 2.60-2.23 (m, 3H), 2.22-2.08 (m, 1H), 1.98-1.81 (m, 1H), 1.80-0.46 (m, 32H).

$^{13}$C NMR: 138.8 (d, J=12.3 Hz), 137.4 (d, J=13.8 Hz), 133.3 (d, J=20.8 Hz), 131.7 (d, J=18.8 Hz), 128.2-126.8 (m), 43.4 (d, J=12.3 Hz), 40.8-39.7 (m), 38.0, 32.8-32.1 (m), 29.7 (d, J=17.6 Hz), 29.0 (d, J=12.3 Hz), 28.9-28.4 (m), 28.0 (d, J=10.3 Hz), 27.1, 27.0-26.0 (m), 25.4 (d, J=17.0 Hz).

$^{31}$P: −3.4 (s), −17.4 (s).

For the examples below, the ligands of the formula (I) are used and are abbreviated as follows:

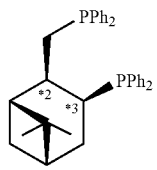

1

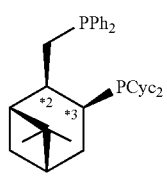

2

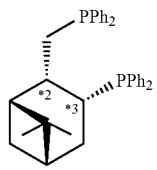

3

-continued

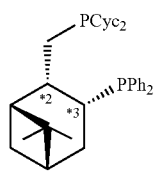

4

Examples 6 to 9

Rhodium-catalysed asymmetric hydrogenation of methyl (Z)-α-acetamidocinnamate

TABLE 1

Rhodium-catalysed asymmetric hydrogenation of methyl (Z)-α-acetamidocinnamate

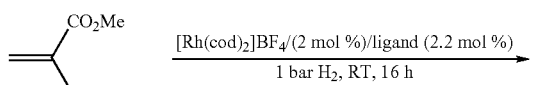

| Example | Ligand | Solvent | T[° C.], t[h] | % ee | Conversion | Yield |
|---|---|---|---|---|---|---|
| 6 | 1 | 1:10 (MeOH:toluene) | 25, 16 | 84 (R) | 100 | 98 |
| 7 | 3 | 1:10 (MeOH:toluene) | 25, 16 | 78 (S) | 100 | 98 |
| 8 | 2 | 1:10 (MeOH:toluene) | 25, 16 | 51 (R) | 100 | 97 |
| 9 | 4 | 1:10 (MeOH:toluene) | 25, 16 | 46 (S) | 100 | 97 |

Examples 10 to 13

Rhodium-catalysed asymmetric hydrogenation of methyl α-acetamidoacrylate

TABLE 2

Rhodium-catalysed asymmetric hydrogenation of methyl α-acetamido-acrylate

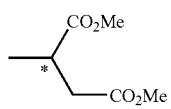

| Example | Ligand | Solvent | T[° C.], t[h] | % ee | Conversion | Yield |
|---|---|---|---|---|---|---|
| 10 | 1 | 1:10 (MeOH:toluene) | 25, 16 | 60 (R) | 100 | 98 |
| 11 | 3 | 1:10 (MeOH:toluene) | 25, 16 | 61 (R) | 100 | 98 |
| 12 | 2 | 1:10 (MeOH:toluene) | 25, 16 | 79 (R) | 100 | 97 |
| 13 | 4 | 1:10 (MeOH:toluene) | 25, 16 | 7 (R) | 100 | 97 |

Examples 14 and 15

Rhodium-catalysed asymmetric hydrogenation of dimethyl itaconate

TABLE 3

Rhodium-catalysed asymmetric hydrogenation of dimethyl itaconate

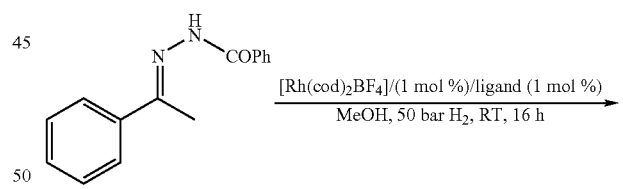

| Example | Ligand | Solvent | T[° C.], t[h] | % ee | Conversion | Yield |
|---|---|---|---|---|---|---|
| 14 | 1 | 1:10 (MeOH:toluene) | 25, 16 | 18 (S) | 100 | 99 |
| 15 | 3 | 1:10 (MeOH:toluene) | 25, 16 | 81 (S) | 100 | 99 |

Example 16

Rhodium-catalysed asymmetric hydrogenation of acetophenone-phenylcarbonyl-hydrazone

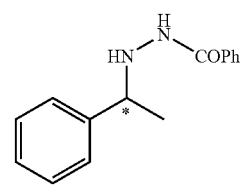

| Example | Ligand | % ee | Conversion | Yield |
|---|---|---|---|---|
| 16 | 1 | 30 (R) | 100 | 88 |

Example 17

Ruthenium-catalysed asymmetric hydrogenation of ethyl 3-phenyl-3-oxopropanoate

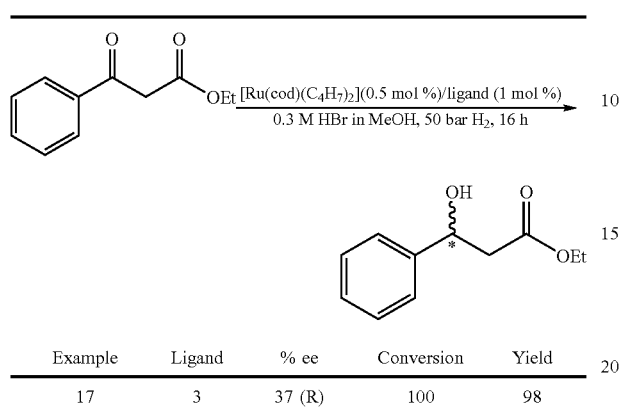

| Example | Ligand | % ee | Conversion | Yield |
|---------|--------|------|------------|-------|
| 17 | 3 | 37 (R) | 100 | 98 |

Example 18

Palladium-catalysed asymmetric allylic substitution of 1,3-diphenylallyl acetate with methyl malonate

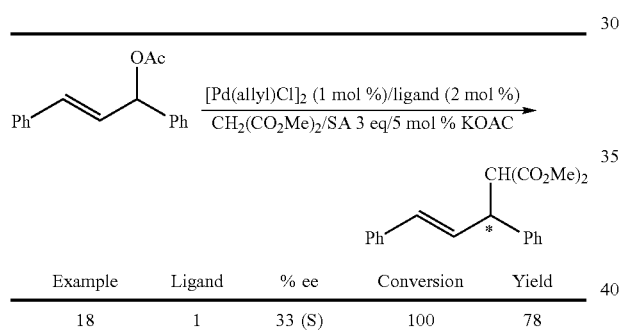

| Example | Ligand | % ee | Conversion | Yield |
|---------|--------|------|------------|-------|
| 18 | 1 | 33 (S) | 100 | 78 |

What is claimed is:

1. Process for preparing compounds of the formula (I)

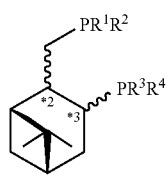

in which
*2 and *3 each mark a stereogenic carbon atom which is in R- or S-configuration, although the substituents are arranged in a cisoid manner based on the connecting carbon bond and
$R^1$, $R^2$, $R^3$ and $R^4$ may each independently be: alkyl, arylalkyl or aryl or a heterocyclic radical having a total of 4 to 16 carbon atoms, or $R^1$ and $R^2$ and/or $R^3$ and $R^4$ each together are alkylene or compounds comprising compounds according to formula I and boranes, characterized in that in a step A), compounds of the formula (IIa) or (IIb)

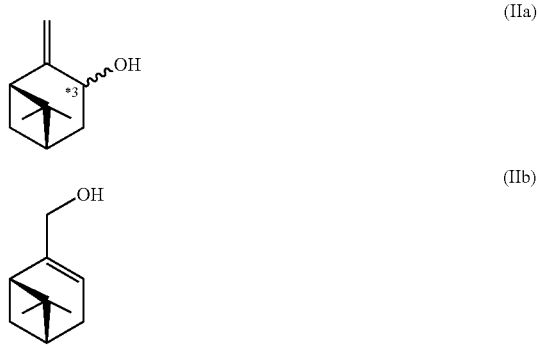

in which *3 has the definitions and areas of preference specified for formula (I)
are reacted with compounds of the formula (IIIa) or (IIIb)

$$\text{Hal-PR}^1\text{R}^2 \quad \text{(IIIa)}$$

$$\text{Hal-PR}^3\text{R}^4 \quad \text{(IIIb)}$$

to give compounds of the formula (IVa) and (IVb)

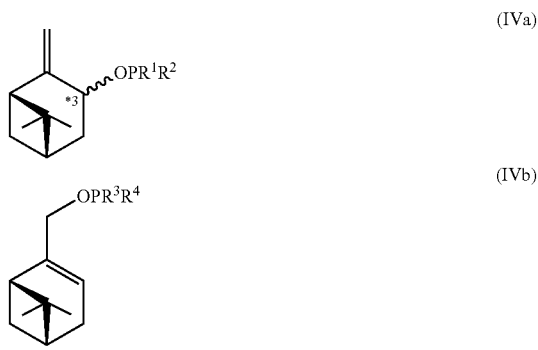

and in a step B), the compounds of the formula (IVa) and (IVb), optionally in an organic solvent, are converted by heating to at least 60 C to compounds of the formula (Va) and (Vb)

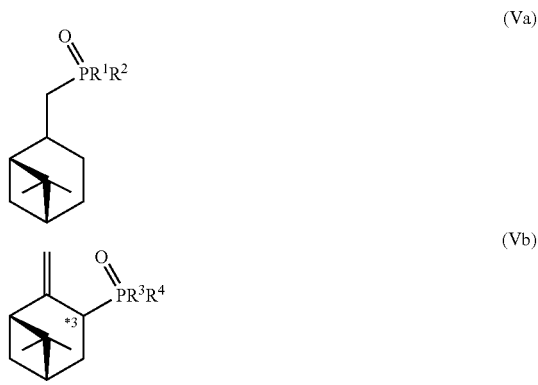

and, in a step C), the compounds of the formula (Va) and (Vb) are converted by reacting with a borane and subsequently oxidizing to compounds of the formula (VIa) and (VIb)

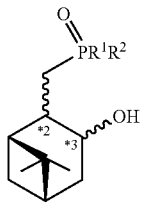

(VIa)

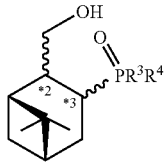

(VIb)

and, in a step D), the compounds of the formula (VIa) and (VIb) are converted by reducing to compounds of the formula (VIIa) and (VIIb)

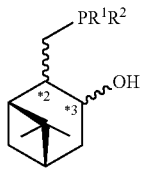

(VIIa)

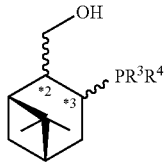

(VIIb)

and, in a step E), the compounds of the formula (VIIa) and (VIIb) are converted by reacting with compounds of the formula (VIII)

Hal-O$_2$SR$^5$ (VIII)

to compounds of the formula (IXa) and (IXb)

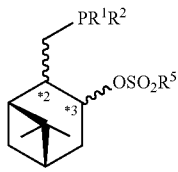

(IXa)

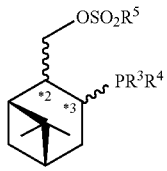

(IXb)

and, in a step F), the compounds of the formula (IX) are converted by reacting with compounds of the formula (Xa) or (Xb)

HPR$^3$R$^4$ (Xa)

HPR$^1$R$^2$ (Xb)

to the compounds of the formula (I), where, in the formulae (IIa), (IIb), (IIIa), (IIIb), (IVa), (IVb), (Va), (Vb), (VIa), (VIb), (VIIa), (VIIb), (IXa), (IXb), (Xa) and (Xb), *2 and *3, R$^1$, R$^2$, R$^3$ and R$^4$ are each defined as has been described in by formula I and R$^5$ in the formulae (VIII), (IXa) and (IXb) is alkyl, fluoroalkyl, arylalkyl or aryl and Hal in the formulae (IIIa) and (IIIb) and (VIII) is in each case chlorine, bromine or iodine.

2. A process for the preparation of compounds of formula I

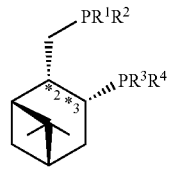

(I)

in which

*2 and *3 each mark a stereogenic carbon atom which is in R- or S-configuration, although the substituents are arranged in a cisoid manner based on the connecting carbon bond and R$^1$, R$^2$, R$^3$ and R$^4$ may each independently be: alkyl, arylalkyl or aryl or a heterocyclic radical having a total of 4 to 16 carbon atoms, or R$^1$ and R$^2$ and/or R$^3$ and R$^4$ each together are alkylene, comprising: converting compounds according to formula (IXa) and (IXb)

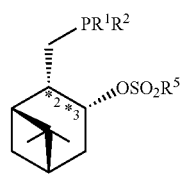

(IXa)

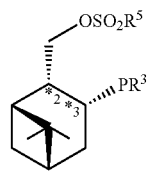

(IXb)

by reacting the compounds of formula (IX) with compounds of the formula (Xa) or (Xb)

HPR$^3$R$^4$ (Xa)

HPR$^1$R$^2$ (Xb)

wherein *2 and *3, R$^1$, R$^2$, R$^3$ and R$^4$ are each defined with respect to formula I, and R$^5$ in formula (IXa) and (IXb) is alkyl, fluoroalkyl, arylalkyl or aryl.

3. A process for the preparation of compounds of the formula (IVa) and (IVb)

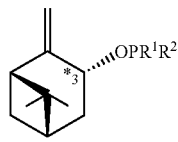
(IVa)

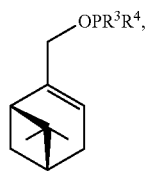
(IVb)

comprising:
reacting compounds of formula (IIa) and (IIb)

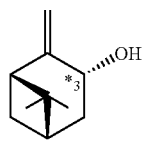
(IIa)

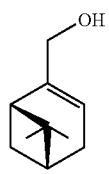
(IIb)

with compounds of the formula (IIIa) or (IIIb)

Hal-PR$^1$R$^2$ (IIIa)

Hal-PR$^3$R$^4$ (IIIb)

wherein,
*3 marks a stereogenic carbon atom which is in R- or S-configuration, although the substituents are arranged in a cisoid manner based on the connecting carbon bond, Hal- is in each case chlorine, bromine or iodine, and R$^1$, R$^2$, R$^3$ and R$^4$ may each independently be alkyl, arylalkyl or aryl or a heterocyclic radical having a total of 4 to 16 carbon atoms, or R$^1$ and R$^2$ and/or R$^3$ and R$^4$ each together are alkylene.

4. A process for the preparation of compounds of formula I

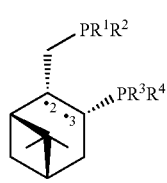
(I)

in which
*2 and *3 each mark a stereogenic carbon atom which is in R- or S-configuration, although the substituents are arranged in a cisoid manner based on the connecting carbon bond and R$^1$, R$^2$, R$^3$ and R$^4$ may each independently be: alkyl, arylalkyl or aryl or a heterocyclic radical having a total of 4 to 16 carbon atoms, or R$^1$ and R$^2$ and/or R$^3$ and R$^4$ each together are alkylene, comprising:

a. reacting compounds of the formula (VIIa) and (VIIb)

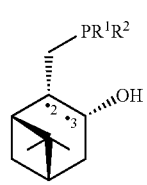
(VIIa)

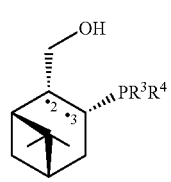
(VIIb)

with compounds of the formula (VIII)

Hal-O$_2$SR$^5$ (VIII)

to form compounds of the formula (IXa) and (IXb)

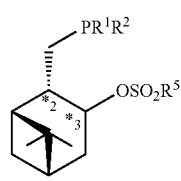
(IXa)

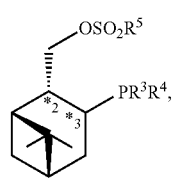
(IXb)

and b. converting compounds according to formula (IXa) and (IXb) to compounds according to formula (I) by reacting the compounds of formula (IX) with compounds of the formula (Xa) or (Xb)

HPR$^3$R$^4$ (Xa)

HPR$^1$R$^2$ (Xb)

wherein *2 and *3, R$^1$, R$^2$, R$^3$ and R$^4$ are each defined with respect to formula I, Hal- is in each case chlorine, bromine or iodine, and R$^5$ in formula (IXa) and (IXb) is alkyl, fluoroalkyl, arylalkyl or aryl.

5. A process for the preparation of compounds of the formula (Va) and (Vb)

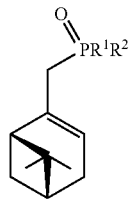
(Va)

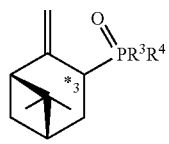
(Vb)

comprising:
a. reacting compounds of the formula (IIa) or (IIb)

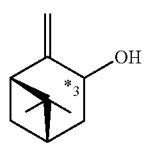
(IIa)

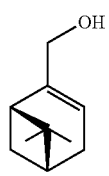
(IIb)

with compounds of the formula (IIIa) or (IIIb)

Hal-PR$^1$R$^2$ (IIIa)

Hal-PR$^3$R$^4$ (IIIb)

to give compounds of the formula (IVa) and (IVb)

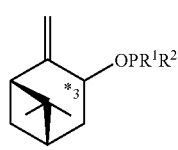
(IVa)

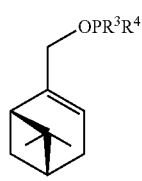
(IVb)

and
b. heating the compounds of the formula (IVa) and (IVb), optionally in an organic solvent, to at least 60 C, wherein, *3 marks a stereogenic carbon atom which is in R- or S-configuration, although the substituents are arranged in a cisoid manner based on the connecting carbon bond, Hal- is in each case chlorine, bromine or iodine, and R$^1$, R$^2$, R$^3$ and R$^4$ may each independently be: alkyl, arylalkyl or aryl or a heterocyclic radical having a total of 4 to 16 carbon atoms, or R$^1$ and R$^2$ and/or R$^3$ and R$^4$ each together are alkylene.

6. The process according to claim 5 further comprising:
reacting the compounds of formula (Va) and (Vb) with a borane and subsequently oxidizing to compounds of the formula (VIa) and (VIb)

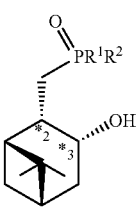
(VIa)

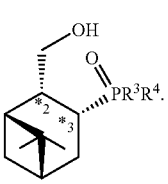
(VIb)

7. The process according to claim 6 further comprising:
a. reducing the compounds of the formula (VIa) and (VIb) to compounds of the formula (VIIa) and (VIIb)

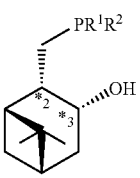
(VIIa)

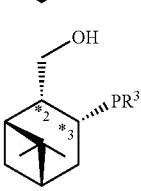
(VIIb)

8. A process for the preparation of compounds of formula I

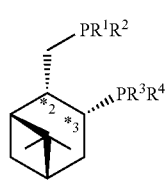
(I)

in which
*2 and *3 each mark a stereogenic carbon atom which is in R- or S-configuration, although the substituents are arranged in a cisoid manner based on the connecting carbon bond and $R^1$, $R^2$, $R^3$ and $R^4$ may each independently be: alkyl, arylalkyl or aryl or a heterocyclic radical having a total of 4 to 16 carbon atoms, or $R^1$ and $R^2$ and/or $R^3$ and $R^4$ each together are alkylene, comprising:

a. reducing the compounds of the formula (VIa) and (VIb)

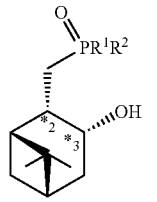

(VIa)

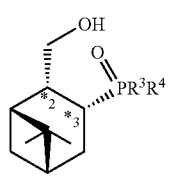

(VIb)

to compounds of the formula (VIIa) and (VIIb)

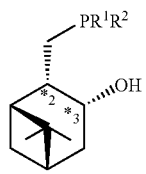

(VIIa)

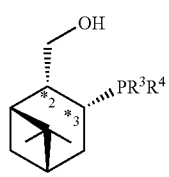

(VIIb)

b. reacting compounds of the formula (VIIa) and (VIIb)

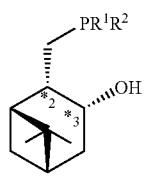

(VIIa)

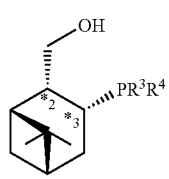

(VIIb)

with compounds of the formula (VIII)

Hal-O$_2$SR$^5$  (VIII)

to form compounds of the formula (IXa) and (IXb)

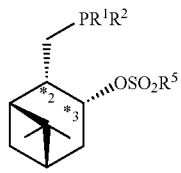

(IXa)

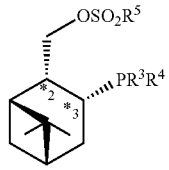

(IXb)

and c. converting compounds according to formula (IXa) and (IXb) to compounds according to formula (I) by reacting the compounds of formula (IX) with compounds of the formula (Xa) or (Xb)

HPR$^3$R$^4$  (Xa)

HPR$^1$R$^2$  (Xb)

where *2 and *3, $R^1$, $R^2$, $R^3$ and $R^4$ are each defined with respect to formula I and $R^5$ in formula (IXa) and (IXb) is alkyl, fluoroalkyl, arylalkyl or aryl.

9. A process for the preparation of compounds of formula I

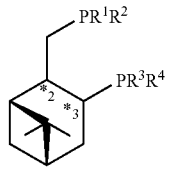

(I)

in which

*2 and *3 each mark a stereogenic carbon atom which is in R- or S-configuration, although the substituents are arranged in a cisoid manner based on the connecting carbon bond and $R^1$, $R^2$, $R^3$ and $R^4$ may each independently be: alkyl, arylalkyl or aryl or a heterocyclic radical having a total of 4 to 16 carbon atoms, or $R^1$ and $R^2$ and/or $R^3$ and $R^4$ each together are alkylene, comprising:

a. reacting the compounds of formula (Va) and (Vb) with a borane and subsequently oxidizing to compounds of the formula (VIa) and (VIb)

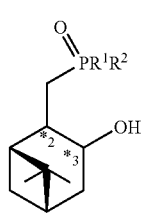

(VIa)

-continued

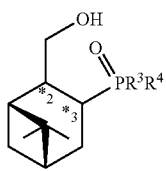
(VIb)

b. reducing the compounds of the formula (VIa) and (VIb) to compounds of the formula (VIIa) and (VIIb)

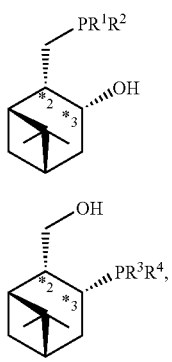
(VIIa)

(VIIb)

c. reacting compounds of the formula (VIIa) and (VIIb) with compounds of the formula (VIII)

Hal-O$_2$SR$^5$   (VIII)

to form compounds of the formula (IXa) and (IXb)

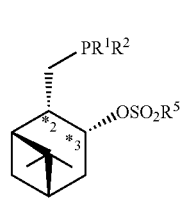
(IXa)

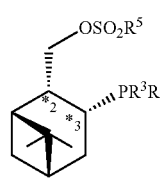
(IXb)

and d. converting compounds according to formula (IXa) and (IXb) to compounds according to formula (I) by reacting the compounds of formula (IX) with compounds of the formula (Xa) or (Xb)

HPR$^3$R$^4$   (Xa)

HPR$^1$R$^2$   (Xb)

wherein *2 and *3, R$^1$, R$^2$, R$^3$ and R$^4$ are each defined with respect to formula I, Hal- is in each case chlorine, bromine or iodine, and R$^5$ in formula (IXa) and (IXb) is alkyl, fluoroalkyl, arylalkyl or aryl.

* * * * *